United States Patent
Ozaki et al.

(10) Patent No.: US 7,031,503 B2
(45) Date of Patent: Apr. 18, 2006

(54) METHOD AND SYSTEM FOR AUTOMATICALLY PRODUCING A TEMPORALLY PROCESSED IMAGE

(75) Inventors: Osamu Ozaki, Amagasaki (JP); Hironori Saki, Amagasaki (JP)

(73) Assignee: Mitsubishi Space Software Co., Ltd., Tokyo (JP)

( * ) Notice: Subject to any disclaimer, the term of this patent is extended or adjusted under 35 U.S.C. 154(b) by 662 days.

(21) Appl. No.: 09/983,599

(22) Filed: Oct. 25, 2001

(65) Prior Publication Data

US 2002/0102014 A1 Aug. 1, 2002

(30) Foreign Application Priority Data

Jan. 31, 2001 (JP) .............................. 2001-023863

(51) Int. Cl.
*G06K 9/00* (2006.01)

(52) U.S. Cl. ...................................... 382/130; 382/132

(58) Field of Classification Search ................ 382/132, 382/130; 711/109, 159, 160, 133
See application file for complete search history.

(56) References Cited

U.S. PATENT DOCUMENTS 5,987,345 A * 11/1999 Engelmann et al. ........ 600/407
6,238,345 B1 * 5/2001 Wissler et al. .............. 600/443
6,373,507 B1 * 4/2002 Camara et al. ............. 345/825
6,526,486 B1 * 2/2003 Theimer ..................... 711/159

FOREIGN PATENT DOCUMENTS

| JP | 5-143700 | 6/1993 |
| JP | 7-37074 | 2/1995 |
| JP | 8-315119 | 11/1996 |
| JP | 9-308612 | 12/1997 |
| JP | 10-155746 | 6/1998 |

* cited by examiner

Primary Examiner—Brian Werner
Assistant Examiner—Christopher Lavin
(74) Attorney, Agent, or Firm—Wenderoth, Lind & Ponack, L.L.P.

(57) ABSTRACT

A system is provided for automatically producing a temporally processed image which includes a storage unit which stores thereon a plurality of radiographic images, the plurality of radiographic images being taken at different points of time. The system is provided with an image input unit for capturing a new radiographic image so as to store the captured new radiographic image on the storage unit and an automatic maintenance control unit for automatically producing, in response to the capture of the new radiographic image, information specifying a predetermined number of pairs of the radiographic images. The specified pairs of the radiographic images includes the captured radiographic image. The system is further provided with an automatic producing unit for automatically producing a specified number of temporally processed images according to the information produced by the automatic maintenance control unit.

18 Claims, 7 Drawing Sheets

METHOD AND SYSTEM FOR AUTOMATICALLY PRODUCING A TEMPORALLY PROCESSED IMAGE

BACKGROUND OF THE INVENTION

1. Field of the Invention

This invention relates to a method and a system for automatically producing a temporally processed image, which are capable of capturing a radiographic image, such as a front chest image into the system and, simultaneously, producing a temporally processed image such as a temporal subtraction image from a plurality of previously designated pairs of radiographic images so as to store the temporally processed image on a data storage unit.

2. Description of Related Art

In a conventional system for producing a temporally processed image, a pair of a current radiographic image and a previous radiographic image (the new image in time is referred to as a "current" image and the old image older than the new image in time is referred to as a "previous" image), such as current and previous front chest images, is captured into the system, and a temporally processed image is produced from the pair of current and previous images.

This technique is disclosed in Japanese Patent Publication No. 7-37074, a method and apparatus for detecting an interval change in temporally sequential chest images, and in Japanese Patent Publication No. 8-110939, an image aligning system and a system for performing processing between images. These techniques are popularly utilized in a research field of computer aided diagnosis.

The above described conventional system for producing a temporally processed image, however, has problems (1)~(3) as follows:

(1) Since the conventional system must capture radiographic images set by set (or designate a pair of radiographic images already captured) so as to produce a temporally processed image, it is a heavy burden for a radiologist, such as a doctor, and requires a lot of time;

(2) In a case where the need for the temporally processed image, previously produced, is eliminated, a radiologist, such as a doctor, has to manually retrieve the temporally processed image to be eliminated so as to manually delete it; and (3) When a doctor or the like manually deletes the temporally processed image, there is the possibility that the doctor or the radiologist unintentionally deletes a temporally processed image, which is not intended to be deleted.

SUMMARY OF THE INVENTION

This invention is directed to overcome the foregoing problems in the conventional art.

Accordingly, it is an object of the present invention to provide a method and system for automatically producing a temporally processed image, which are capable of automatically producing a temporally processed image when radiographic images are captured into the system so as to reduce an amount of work for diagnostic readings and shorten an elapsed time for diagnostic readings.

Another object of the present invention, in addition to the above object, is to provide a method and a system for automatically producing a temporally processed image, which are capable of preventing the temporally processed image to be saved from being unintentionally deleted.

A further object of the present invention, in addition to the above objects, is to provide a method and a system for automatically producing a temporally processed image, which can automatically delete the temporally processed image, which is not required for the diagnostic readings.

To achieve such objects, according to a first aspect of the present invention, there is provided a method for automatically producing a temporally processed image, the method comprising the steps of:

preparing a storage unit, the storage unit storing thereon a plurality of radiographic images, the plurality of radiographic images being taken at different points of time;

capturing a new radiographic image; and automatically producing, in response to the capturing step, a specified number of temporally processed images according to a predetermined number of pairs of the radiographic images, the pairs of the radiographic images including the captured radiographic image, the predetermined number of pairs of the radiographic images being previously specified.

The term "radiographic image" used herein is employed to mean "digitized image which is produced by digitizing a radiographic obtained by transmitting a radiation through a human body" such as a front chest image, a lateral chest image thereof and so on.

In addition, the term "temporally processed image" used herein is employed to mean "image obtained by performing image processing with using two radiographic images" such as a temporal subtraction image, energy subtraction image and so on.

Furthermore, the term "temporal subtraction image" used herein is employed to mean "subtraction image" produced by processing two radiographic images which are taken at different points of time with the use of algorism such as "temporal subtraction method". On the temporal subtraction image, it is possible to enhance an interval change portion occurring in the two radiographic images. Incidentally, the technique of producing the temporal subtraction image is disclosed in Japanese Patent Publication No. 7-37074.

Still further, the term "energy subtraction image" used herein is employed to mean "subtraction image between two radiographic images which are obtained by using different voltages of an X-ray tube." By obtaining the difference (difference absorbability of X-ray) between the two radiographic images which are obtained by using different voltages of the X-ray tube, it is possible to enhance conditions of each of the tissues of the human body, including bones, vessels and the like.

In preferred embodiment of the first aspect, the new captured radiographic image and the produced number of temporally processed images are stored on the storage unit.

According to the first aspect of the present invention, it is possible to omit labor required for individually specifying each of the radiographic images to produce the temporally processed image, making it possible to reduce the burden of a doctor or a radiologist which performs diagnostic readings of the number of temporally processed images.

Moreover, because the temporally processed image is automatically produced, it is possible to quickly extract the temporally processed image to which the doctor or radiologist wishes to refer to so as to reduce a time required for producing the temporally processed image.

In a preferred embodiment of the first aspect, the paired radiographic images in the automatically producing step are composed so that a latest radiographic image and a predetermined number of previous radiographic images are paired, the latest radiographic image being taken at a latest point of time, the predetermined number of previous radiographic images being taken at points of time sequentially before the latest radiographic image is taken.

According to the preferred embodiment of the first aspect, it is possible to recognize the recent interval change.

In the preferred embodiment of the first aspect, the paired radiographic images in the automatically producing step are composed so that the new captured radiographic image and the radiographic images are paired, the radiographic images being permitted to be paired to the new captured radiographic image.

According to the preferred embodiment of the first aspect, it is possible to produce temporally processed images without omission.

The first aspect of the present invention has an arrangement that, in a case where the new captured radiographic image is one of the previous radiographic images, the paired radiographic images in the automatically producing step are composed so that the new captured radiographic image and the latest radiographic image are paired, and in a case where the new captured radiographic image is the latest radiographic image, the paired radiographic images in the automatically producing step are composed so that the new captured radiographic image and the predetermined number of previous radiographic images are paired.

According to the arrangement of the first aspect, it is possible to reduce the burden with respect to a system performing the method.

The first aspect of the present invention has an arrangement that the automatically producing step comprises a step of determining whether or not one of the temporally processed images to be produced is stored on the storage unit so as not to produce the one of the temporally processed images in the case where the one of the temporally processed images is already produced to be stored on the storage unit.

According to the arrangement of the first aspect, it is possible to make further reduce the burden with respect to a system performing the method.

The first aspect of the present invention has an arrangement which includes, in response to the capturing step, a step of automatically deleting at least one of the temporally processed images from the storage unit, the one of deleted temporally processed images becoming unnecessary.

According to the arrangement of the first aspect, it is possible to reduce the burden of the administration operation by a system administrator, such as an operation of arranging a disk.

In the preferred embodiment of the first aspect, the one of the deleted temporally processed images overflows from the predetermined number of pairs of the radiographic images.

According to the preferred embodiment of the first aspect, it is possible to automatically delete the overflowed temporally processed images from the predetermined number of pairs of the radiographic images one after another whenever the new radiographic image is captured, thereby simplifying the system configuration of performing the method.

The first aspect of the present invention has an arrangement which includes a step of setting at least one of the temporally processed images stored on the storage unit to be protected so that the at least one of protected images is prevented from being deleted, wherein the protected images are permanently stored on the storage unit.

According to the arrangement of the first aspect, it is possible to prevent a doctor or a radiologist from accidentally deleting the temporally processed image or the source images (current image and previous image) thereof, which are related to an academic case the doctor or radiologist encounters during diagnostic readings.

For achieving such objects, according to a second aspect of the present invention, there is provided a system for automatically producing a temporally processed image, the system comprising:

a storage unit which stores thereon a plurality of radiographic images, the plurality of radiographic images being taken at different points of time;

means for capturing a new radiographic image;

first production means for automatically producing, in response to the capture of the new radiographic image, information specifying a predetermined number of pairs of the radiographic images, the specified pairs of the radiographic images including the captured radiographic image; and second production means for automatically producing a specified number of temporally processed images according to the information produced by the first production means.

In a preferred embodiment of the second aspect, the new captured radiographic image and the produced number of temporally processed images are stored on the storage unit.

According to the second aspect of the present invention, it is possible to reduce the burden of a doctor or a radiologist which performs diagnostic readings of the number of temporally processed images.

A preferred embodiment of the second aspect comprises means for storing thereon the information produced by the first production means.

According to the second aspect of the present invention, it is possible to deal with a case that the radiographic images sequentially are captured.

In the preferred embodiment of the second aspect, the plurality of radiographic images are obtained from a patient by taking images of the patient at different points of time, the patient having identification information, each of the radiographic images having identification information, wherein the storage unit stores the identification information of the patient related to each of the radiographic images and the temporally processed images, wherein each of the identification information of each of the radiographic images and the temporally processed images and each point of time of taking the images of each of the radiographic images, and wherein the first production means comprises a detecting unit for detecting that the new radiographic image is captured by the capturing means, a unit for extracting the identification information of the patient corresponding to the new radiographic image detected by the detecting unit, a unit for obtaining the identification information of the radiographic images, the taking points of time thereof and previous radiographic images from the storage unit, each of the identification information of the radiographic images, the taking points of time thereof and the previous radiographic images corresponding to the extracted identification information of the patient, the previous radiographic images being previously stored on the storage unit and a unit for producing the information specifying the predetermined number of pairs of the radiographic images according to a number of the previous radiographic images.

According to the second aspect of the present invention, it is possible to quickly search the temporally processed images.

The second aspect of the present invention has an arrangement that the first production means determines whether or not one of the temporally processed images to be produced is stored on the storage unit, in the case where the one of the temporally processed images is already produced to be stored on the storage unit, so as not to produce the information specifying at least one of pairs of the radiographic images, the one of pairs of the radiographic images corresponding to one of the temporally processed image which has already been produced.

According to the second aspect of the present invention, it is possible to reduce the load with respect to the system.

The second aspect of the present invention has an arrangement that the first production means, in response to the capture of the new radiographic image, produces deleting information specifying at least one of the temporally processed images which becomes unnecessary, further comprising means for automatically deleting, in response to the capture of the new radiographic image, at least one of the temporally processed images from the storage unit on the basis of the produced deleting information.

According to the second aspect of the present invention, it is possible to reduce the burden of the administration operation by a system administrator, such as an operation of arranging a disk.

The second aspect of the present invention has an arrangement of further comprising means for setting at least one of the temporally processed images stored on the storage unit to be protected so that the at least one of protected images is prevented from being deleted and means for releasing the protected state of the at least one of the temporally processed images.

According to the second aspect of the present invention, it is possible to prevent a doctor or a radiologist from accidentally deleting the temporally processed image or the source images (current image and previous image) thereof, which are related to an academic case the doctor or radiologist encounters during diagnostic readings.

BRIEF DESCRIPTION OF THE DRAWINGS

Other objects and aspects of the present invention will become apparent from the following description of an embodiment with reference to the accompanying drawings in which.

DESCRIPTION OF THE PREFERRED EMBODIMENTS

The preferred embodiments of the present invention will be described hereinafter with reference to the accompanying drawings.

Figure 1:
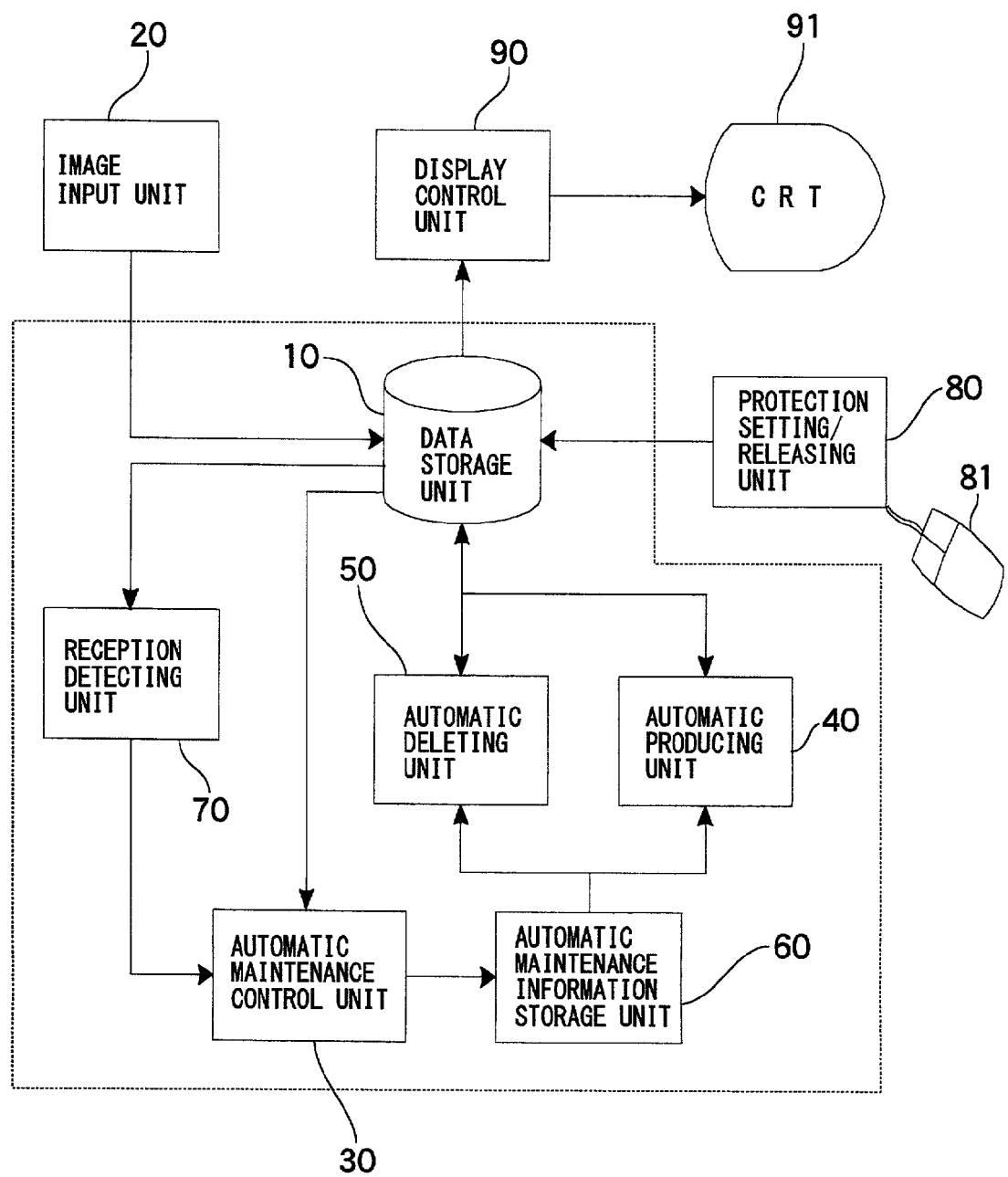
FIG. 1 is a configuration view showing an automatically producing system for a temporally processed image according to a first embodiment of the present invention.

FIG. 1 shows a system configuration of an automatic producing system for producing a temporally processed image according to an embodiment of the present invention. This embodiment describes a case of producing a temporal subtraction image as a temporally processed image from radiographic images such as a front chest image of a patient.

The front chest image, which is also called a PA (postero-anterior) image, is a digitized radiograph thereof, that is obtained by irradiating X-ray from a back side of the chest. Incidentally, an AP (anterior-postero) chest image is obtained by irradiating X-ray from a front side of the chest.

Moreover, the temporal subtraction image is an image obtained by performing an image processing technique (this technique is called a "temporal subtraction method" and described in Japanese Patent Publication No. 7-37074 and so on). That is, the temporal subtraction image is produced by subtracting a previous front chest image of the chest from a current front chest image thereof (the new image in time is referred to as a "current" image and the old image is referred to as a "previous" image) so as to eliminate the normal tissues which are common to these current and previous images thereby enhancing only a new lesion portion or an interval change in known lesion.

The automatic producing system of a temporally processed image according to the present invention comprises a data storage unit 10, an image input unit 20 for inputting a front chest image of a patient (hereinafter, referred simply to "chest image") into the data storage unit 10 and an automatic maintenance control unit 30 operative to generate information related to at least one pair of chest images as information for automatically producing at least one temporal subtraction image simultaneously when a new chest image is captured into the data storage unit 10 from the image input unit 20.

The automatic producing system also comprises an automatic producing unit 40 which operates to automatically produce, on the basis of the produced automatic producing information by the automatic maintenance control unit 30, a designated number of temporal subtraction images so as to store the produced number of temporal subtraction images on the data storage unit 10.

The at least one pair of chest images means at least one pair of one of the current chest images and one of the previous chest images. For example, in a case of producing N temporal subtraction images, N pairs of chest images are required and the N pairs of chest images include N current chest images and N previous chest images, respectively.

The system also comprises an automatic deleting unit 50 for deleting a temporally processed image which becomes unnecessary, every time the new temporally processed image is captured into the data storage unit 10. The automatic maintenance control unit 30 also generates, every time the new temporally processed image is captured into the data storage unit 10, automatically deleting information related to the unnecessary temporal subtraction image so that the automatic deleting unit 50 deletes the unnecessary temporally processed image from the data storage unit 10 based on the automatically deleting information generated by the automatic maintenance control unit 30.

The automatically producing information and automatically deleting information, both generated by the automatic maintenance control unit 30, are combined together into image maintenance information, and the image maintenance information is stored in an automatic maintenance information storage unit 60.

The data storage unit 10 stores a plurality of chest images taken at different points of time and temporal subtraction images produced with a combination of the chest images.

The data storage unit 10 stores image data including not only chest images inputted from the image input unit 20 but also temporal subtraction images generated by the automatic producing unit 40, and so on.

The data storage unit 10 also stores each patient ID (identification) as patient identifying information corresponding to each image data, each image ID (source ID in case of temporal subtraction image) as image identifying information corresponding to each image data, each taking time (date and time) corresponding to each chest image and protection information. Contents of this information is not limited and thus, may be customized according to the system.

The source ID means an ID which can uniquely identify the source pair of the current chest image and the previous chest image. In this embodiment, the source ID of the source pair of the current and previous images is derived when the temporal subtraction image corresponding to the current and previous images is generated so that the source ID is an equivalent with the ID of the temporal subtraction image.

A number of previous cases, information for specifying whether automatically deleting is to be performed or not, and information for specifying one of methods of automatically producing a temporal subtraction image are stored previously in the data storage unit 10.

The image input unit 20 is operative to digitize the taken chest X-ray radiograph. The digitized chest X-ray radiograph is stored as the chest image in the data storage unit 10 of this system.

In the case of digitizing a chest radiograph, image input unit 20 includes a device for digitizing a film such as a film digitizer or the like, and in the case of digitally taking a chest radiograph, input image unit 20 includes a digital imaging unit, such as a CR (computed radiography) unit. Any device or unit can be used whenever the chest image can be produced.

The automatic producing system also comprises a reception detecting unit 70 which can communicate with the data storage unit 10 and the automatic maintenance control unit 30. The reception detecting unit 70 is operative to detect that the chest image inputted from the image input unit 20 is received by the data storage unit 10 so as to be stored thereon, thereby transmitting the reception information of the chest image to the automatic maintenance control unit 30.

According to the patient ID of the received chest image by the reception detecting unit 70, the automatic maintenance control unit 30 obtains an ID of the chest image of the patient, a time of taking the image and the number of the previous cases from the data storage unit 10.

The automatic maintenance control unit 30 then produces the automatic maintenance information including the automatic producing information designating at least one pair of chest images by which at least one temporal subtraction image is to be automatically produced (the image producing information of the temporal subtraction image) and the automatic deletion information (the image deleting information of the temporal subtraction image) designating the temporal subtraction image which is to be automatically deleted, so as to output the generated automatic maintenance information to the storage unit 60. The storage unit 60 receives the outputted automatic maintenance information to store it thereon.

The automatic producing unit 40 automatically produces the temporal subtraction image on the basis of the automatic producing information stored on the storage unit 60 so as to output the produced temporal subtraction image to the data storage unit 10.

The automatic deleting unit 50 automatically deletes the temporal subtraction image from the data storage unit 10 according to the automatic deleting information stored in the automatic maintenance information storage unit 60.

In the processing of deleting the temporal subtraction image, when the protection information corresponding to the temporal subtraction image subjected to delete is set as "setting", the corresponding temporal subtraction image is not deleted. The protection information is information for protecting the corresponding temporal subtraction image concerned with an important case with which the radiologist or the like encountered during reading of the image, so as not to be automatically deleted by this system.

In order to enable and disable the protection function, a protection setting/releasing unit 80 is provided for the system. The protection setting/releasing unit 80 processes the request designated from an input device 81 so as to perform the processing for rewriting the protection information of the corresponding temporal subtraction image stored in the data storage unit 10 to "setting" or "releasing".

The input device 81 transmits the request for setting the protection information of the temporal subtraction image. A mouse is generally used as this device, however a touch pen, a keyboard or other similar devices can be substituted.

The corresponding temporal subtraction image denotes the temporal subtraction image as the target for rewriting the protect information. The corresponding temporal subtraction image is previously selected through a man-machine interface (MMI/F), such as a GUI (graphical user interface), displayed in a display (CRT) 91.

When protecting the temporal subtraction image, the corresponding temporal subtraction image is not deleted automatically, and at the same time, the source images (the current and previous chest images), from which the corresponding temporal subtraction image is produced, are protected (are not deleted).

When the protection information is set to a "setting" state, the corresponding temporal subtraction image to the protection information is set to be in a protected state so that the temporal subtraction is prevented from being deleted.

In a case where the protection information is set to a "releasing" state, the corresponding temporal subtraction image to the protection information is set to be in an unprotected state so that the temporal subtraction image is permitted to be automatically deleted. The "releasing" is used as the reverse meaning of "setting" herein so that the protection information is not set to "setting".

In a case where the image data is stored as a file in the data storage unit 10, the property information of the stored image file can be utilized for the protection information. Thus, the property information is set to "read only" state so that it is possible to set the protection information to "setting". However, regardless of whether the image data is a file format or not, providing a storage area capable of storing thereon the protection information corresponding to each information data in a data storing area of the data storage unit 10, such as a database, it is possible to generalize the setting of the protection information. In this embodiment, the latter system is employed.

The images stored in the data storage unit 10 are read out in response to the requirement of readings transmitted from the input device 91, and the read out images are controlled by display control unit 90 to be displayed on the display (CRT) 91.

The display control unit 90 controls the image data on the screen of the display 91, which is selectively specified by the man-machine interface, such as the GUI. In this embodiment, as the display, the CRT is used, but a plasma display unit, a liquid crystal display unit or other similar display units may be used as the display 91. In this embodiment, it is preferable that the CRT having high resolution, such as 1000 scanning lines class or more is used, because this system is a medical system.

In the system, according to this embodiment, for automatically producing the temporal subtraction image simultaneously when the new chest image is captured into the system, a designated number of temporal subtraction images is automatically produced from a plurality of previously designated pairs of chest images so as to be stored on the data storage unit 10.

Next, the automatic maintenance information produced in the automatic maintenance control unit 30 will be described.

The automatic maintenance information includes (1) the automatic producing information of the temporal subtraction image and (2) the automatic deleting information of the temporal subtraction image.

The automatic producing information includes the following information:

information (1-1) of the numbers M of the temporal subtraction images to be produced;

information (1-2) of the IDs of the current chest images which are the sources of the M temporal subtraction images to be produced; and information (1-3) of the IDs of the previous chest images which are the sources of the M temporal subtraction images to be produced.

The information (1-2) and (1-3) are equivalent to the M pairs of the current chest images and the previous chest images which are the sources of the M temporal subtraction images.

The automatic deleting information comprises the following information:

information (2-1) of the numbers N of the temporal subtraction images to be deleted;

information (2-2) of the IDs of the N temporal subtraction images to be deleted; and information (2-3) of the protection information of the N temporal subtraction images to be deleted.

In this embodiment, the information (data) of (2-2) designates the source IDs of the pairs of the current and previous chest images, which are generated when the corresponding temporal subtraction images are produced.

Figure 2:
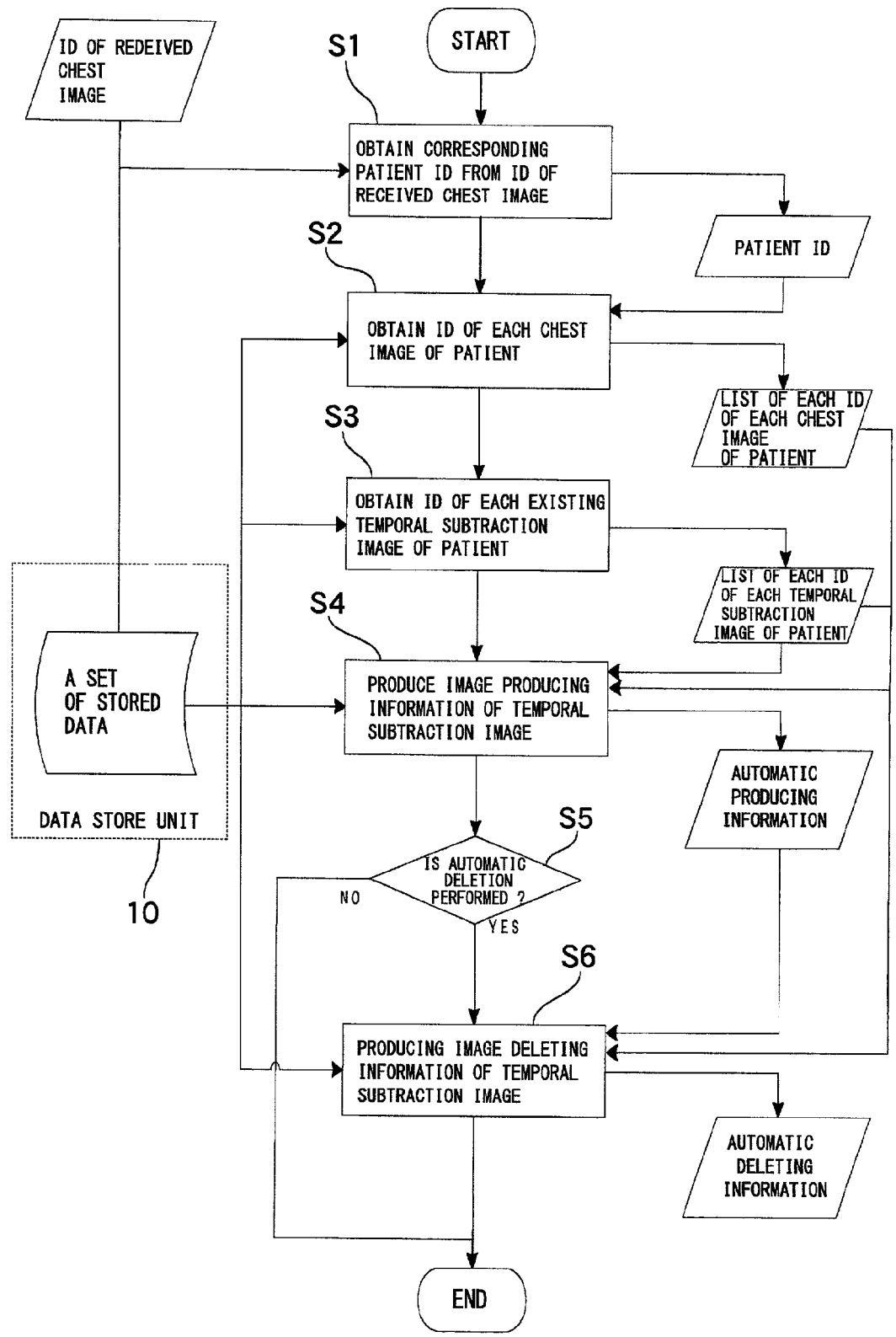
FIG. 2 is a flow chart showing a processing procedure of producing automatic maintenance information by an automatic maintenance control unit shown in FIG. 1.

The method for producing the automatic maintenance information will now be described according to the flowchart of FIG. 2.

(Step S1)

From the ID of the chest image, the reception of which is detected by the reception detecting unit 70, the corresponding patient ID of the received chest image is obtained by the automatic maintenance control unit 30.

That is, the producing of the automatic maintenance information is started by the control unit 30 in response to the reception of the data from the reception detecting unit 70. When the reception of the chest image is detected, at the same time, the ID of the received image is recognized whereby the patient ID corresponding to the chest image is retrieved by the control unit 30 from the data storage unit 10.

In this embodiment, the patient ID is stored with the chest image. Therefore, in a case where the ID of the received chest image is recognized, the corresponding patient ID can be obtained easily.

(Step S2)

The IDs of the chest images of the patient are obtained by the control unit 30.

All of the IDs of the chest images concerned with the patient ID obtained at step S1 are extracted by the control unit 30 from the data storage unit 10 so that the ID list of the chest images corresponding to the patient ID is produced by the control unit 30.

(Step S3)

The IDs of the existing temporal subtraction images are obtained by the control unit 30.

Similarly, all of the IDs of the temporal subtraction images concerned with the patient ID obtained at step S1 are obtained by the control unit 30 so that the ID list of the temporal subtraction images corresponding to the patient ID is produced thereby.

(Step S4)

The image producing information of the temporal subtraction image is produced by the control unit 30.

The number N of previous cases and the automatic producing method T stored previously in the system are obtained by the control unit 30 from the data storage unit 10, and moreover, pairs of the chest images which are the sources of the temporal subtraction images are selectively set according to the ID list obtained at step S2 and the ID list obtained at step S3.

The set pairs of the chest images and the number of the set pairs of the chest images provide the image producing information of the temporal subtraction image.

(Step S5)

Whether automatic deletion is performed or not is determined by the control unit 30.

Every time the chest image is received by the reception detecting unit 70, the control unit 30 performs the switching processing so as to determine whether the temporal subtraction image overflowed from the number of previous cases is deleted or not.

That is, the information B designating whether or not the automatic deletion is performed stored previously in the data storage unit 10 is obtained therefrom by the control unit 30 so that, in a case where the information B designates "ON" wherein the automatic deletion is performed, the process of the control unit 30 is shifted to step S6 for generating the image deleting information. On the other hand, in a case where the information B designates "OFF" wherein the automatic deletion is not performed, the number of the temporal subtraction images to be deleted contained in the image deleting information is set to 0 by the control unit 30 so that the process thereof is terminated.

This automatic deletion designating information B is stored previously in the data storage unit 10.

(Step S6)

The image deleting information is produced by the control unit 30.

The number N of previous cases stored previously in the data storage unit 10 is obtained therefrom by the control unit 30, and the temporal subtraction image to be deleted automatically is chosen by the control unit 30 on the basis of the ID lists obtained at steps S2 and S3. At the same time, the protection information corresponding to the chosen temporal subtraction image is obtained by the control unit 30 and the protection information is set thereby as a part of the image deleting information.

Next, referring to FIG. 3, examples of producing the image producing information and the image deleting information described in steps S4 and S6 of the flowchart will be described in detail.

For the automatic producing method, a variety of producing methods can be utilized. In addition, simultaneously to when the chest image is received, a temporal subtraction image is produced in combination of the images corresponding to the number of previous cases.

In this embodiment, the following methods 1 and 2 are among the simplest methods employed. It is preferred that these methods be performed after being customized in accordance with the request.

Method 1:

At least one of the temporal subtraction images is automatically produced according to a part of the chest images which are permitted to be paired to the received chest image.

Method 2:

At least one of the temporal subtraction images is automatically produced according to only a pair of the latest current chest image and the received chest image.

The designation information of designating one of the automatic producing methods is previously stored in the system.

In this embodiment, although the automatic deletion is performed in accordance with the automatic producing method, by previously setting the automatic deletion method for the system, the automatic deletion can be performed independent from the automatic producing method.

First, the automatic producing method 1 and the rules of the automatic deletion corresponding to method 1 will be described.

In this embodiment, the number of previous cases for producing a temporal subtraction image is 4.

In the description hereinafter, the latest image is employed to mean the chest image whose chest X-ray front radiograph has the latest taking point of time, and the previous image is employed to mean the chest image other than the latest image.

In addition, the number of previous cases is employed to mean the number of previous images, and "the number N of previous cases" is employed to mean the latest N previous images with reference to the taking points of time.

In this embodiment, the number of previous cases is stored in the system previously.

Figure 3A:
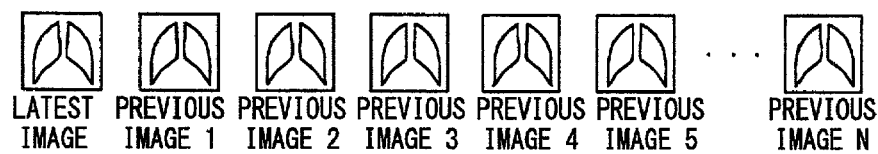
FIG. 3A is a conceptional view showing an example of automatic producing information and automatic deleting information by using an automatic producing method 1.
Figure 3B:
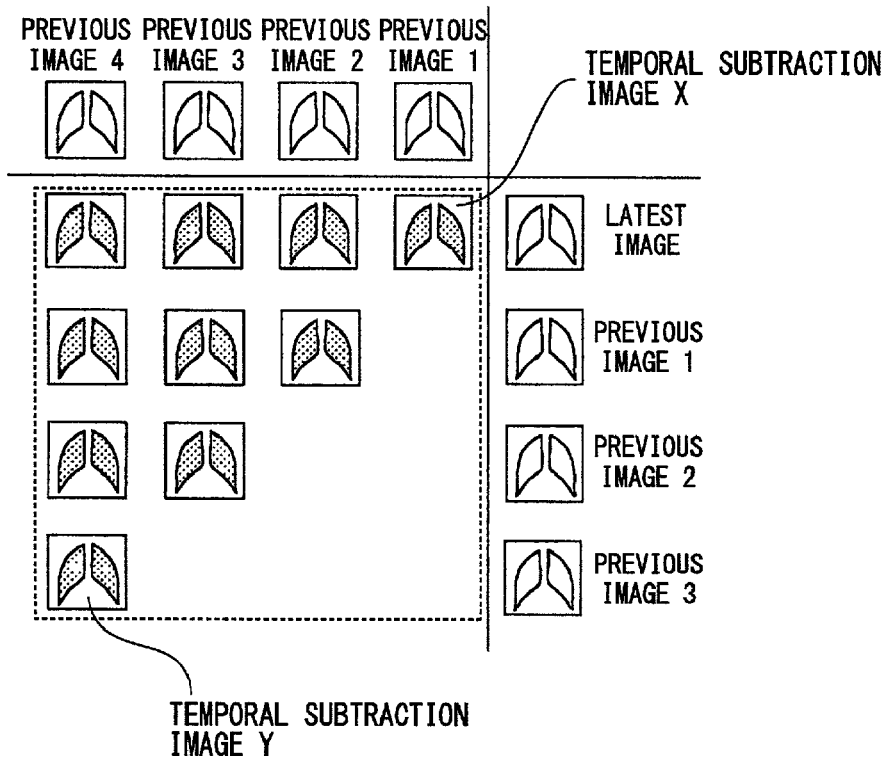
FIG. 3B is a conceptional view showing the example of the automatic producing information and the automatic deleting information by using the automatic producing method 1.

FIGS. 3A and 3B show the state prior to receiving the chest image.

FIG. 3A shows a list in which chest images (the latest image, the previous image 1, the previous image 2, . . . , the previous image n) of a certain patient A are temporally sequentially aligned, and FIG. 3B represents the matrix arrangement of the temporal subtraction images automatically produced under the condition that the number N of previous cases is 4.

Previous images 1 through 4 corresponding to the number N of previous cases are the previous cases to be automatically produced so that the latest image and the previous images 1 to 4 are composed to be paired thereby producing the temporal subtraction images on the basis of the paired images, respectively.

For example, the temporal subtraction image X is to be produced on the basis of the pair of the latest image and the previous image 1, and the temporal subtraction image Y is to be produced on the basis of the pair of the previous image 3 and the previous image 4.

Figure 4A:
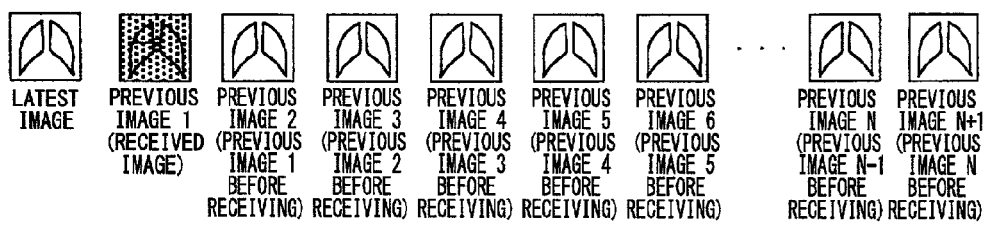
FIG. 4A is a conceptional view showing the example of the automatic producing information and the automatic deleting information by using the automatic producing method 1.
Figure 4B:
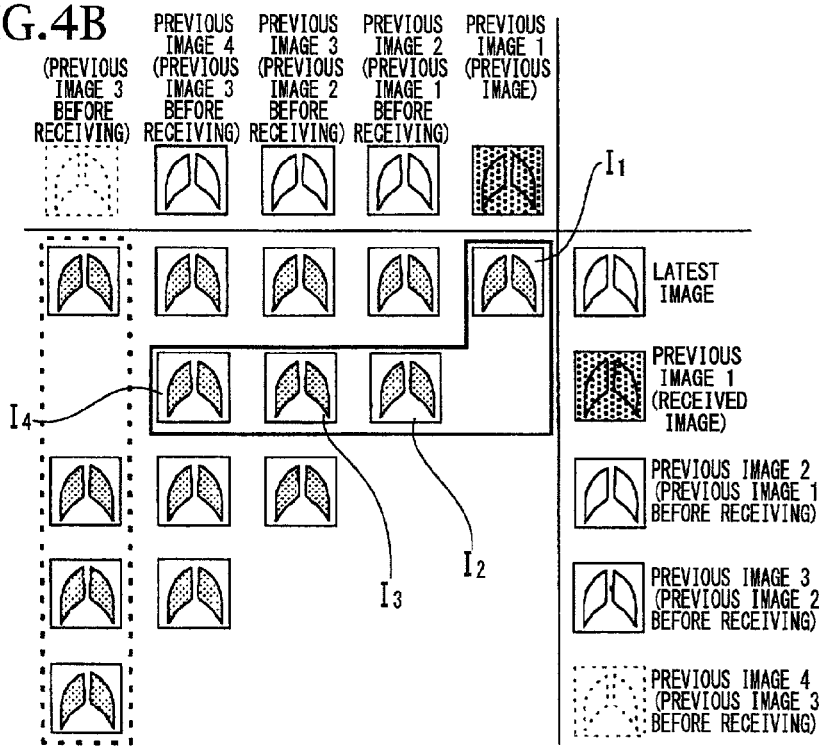
FIG. 4B is a conceptional view showing the example of the automatic producing information and the automatic deleting information by using an automatic producing method 1.

FIGS. 4A and 4B show the state after receiving the chest image.

FIG. 4A shows a list of chest images after receiving the new chest image. The previous image 1 is the received chest image and the previous image n after receiving is the previous image (n−1) before receiving.

The temporal subtraction images are produced according to a part of the chest images which are permitted to be paired to the new received chest image.

That is, the new received image is paired with each of the latest image and the previous images 1–4 except for the previous image 1 after receiving, because the previous image 1 corresponds to the new received image so that it is impossible to pair the new received image with the previous image 1, whereby the four temporal subtraction images are to be automatically produced.

In FIG. 4B, the four temporal subtraction images surrounded with a squared solid line are the temporal subtraction images to be automatically and newly produced under the condition that the number N of previous cases is 4.

That is, the temporal subtraction image I1 is to be produced based on the pair of the new received image and the latest image, and the temporal subtraction image I2 is to be produced based on the pair of the new received image and the previous image 2. Similarly, the temporal subtraction image I3 is to be produced based on the pair of the new received image and the previous image 3, and the temporal subtraction image I4 is to be produced based on the pair of the new received image and the previous image 4.

Moreover, the temporal subtraction images surrounded with a squared broken line are the temporal subtraction images to be automatically deleted, which are overflowed from the condition that the number N of previous cases is 4, because the temporal subtraction images I1–I4 are newly produced under the condition that the number N of previous cases is 4.

The received image is not only the latest chest image (the latest image) in time series, but also, for example, the receiving of the image data of the second order in time series is considered as this embodiment. Of course, it is possible that the received image is the latest chest image (latest image) in time series.

However, in a case where the received chest image is the fifth order or more in time series older than the previous image 4, automatically producing the temporal subtraction images is not performed because the condition of the automatic producing and automatic deleting (the subjected number N of previous cases is 4) is not satisfied.

The idea of this automatic producing method 1 is as follows.

The number of the temporal subtraction images to be automatically produced is 4 in the embodiment described above. Although 10 temporal subtraction images essentially can be produced as a maximum on the basis of ten pairs of the latest image and the previous images 1 to 4, because 6 images in the 10 images are the same as the temporal subtraction images already obtained before receiving the new chest image, the system is adapted to prevent the repeated production of the temporal subtraction images.

This is intended to minimize the burden of the system, and the higher the number N of previous cases, the more this effect can be obtained.

In the embodiment, since the number N of previous cases is 4, and the 6 temporal subtraction images are automatically produced to be overlapped, the burden for the system is not as large as compared with all combinations of the 10 frames. However, in a case where the number N of previous cases is 100, the 4950 temporal subtraction images are automatically produced to be overlapped so that most of the burden of the system is wasted on producing overlapped images.

(Prevention of Overlapped Production)

In the embodiment of this system, the ID of the temporal subtraction image (image ID) is stored in the data storage unit 10 as the source ID.

When automatically producing the temporal subtraction image, this source ID is used so as not to newly produce the same temporal subtraction image as has already been produced.

The ID of the temporal subtraction image (source ID) is defined as "the ID of the current chest image +"#"+ the ID of the previous chest image", and whether the temporal subtraction image, which is intended to be produced, is the existing temporal subtraction image or not, is checked by the ID of the temporal subtraction image stored in the data storage unit 10 so as not to produce overlapped images.

In this case, in a case where the ID of temporal subtraction image intended to be produced is found in the data storage unit 10 by collation processing, the corresponding temporal subtraction image is not produced.

Since the ID of the current chest image and the ID of the previous chest image are unique in the system, respectively, it is possible to ensure that the IDs of the temporal subtraction images (source IDs) produced by the IDs of the current and previous chest images are also unique.

Thus, in this embodiment, the concept of the source ID is introduced as the method for checking whether the temporal subtraction image to be produced already exists in the data storage unit 10 or not. However, in a case where the temporal subtraction image can be specified uniquely and the ID of the current chest image and the ID of the previous chest image, as the source of the temporal subtraction image, can be specified, even if the file of the temporal subtraction image is stored in the data storage unit 10, it is possible to securely recognize whether the temporal subtraction image to be produced already exists in the data storage unit 10 or not by checking the file name, the presence or absence of the file and the like.

Next, referring to FIG. 5, method 2 and the rules of the automatic deletion of that will be described.

The state before receiving the chest image is the same as in the automatically producing method as shown in FIGS. 3A and 3B.

Figure 5A:
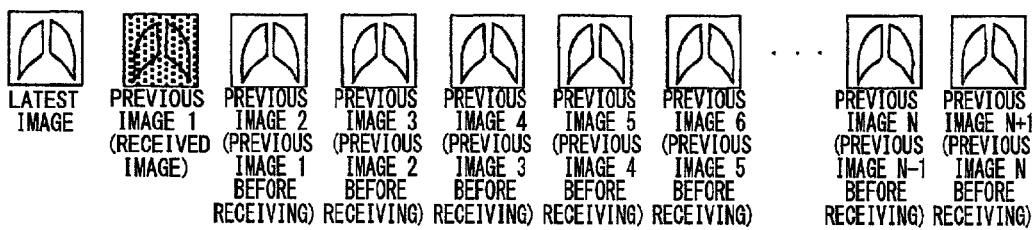
FIG. 5A is a conceptional view showing an example of automatic producing information and automatic deleting information by using an automatic producing method 2.

FIG. 5A shows a list of chest images after receiving the new received chest image. The previous image 1 is the received image and the previous image n after receiving is the previous image (n−1) before receiving.

Figure 5B:
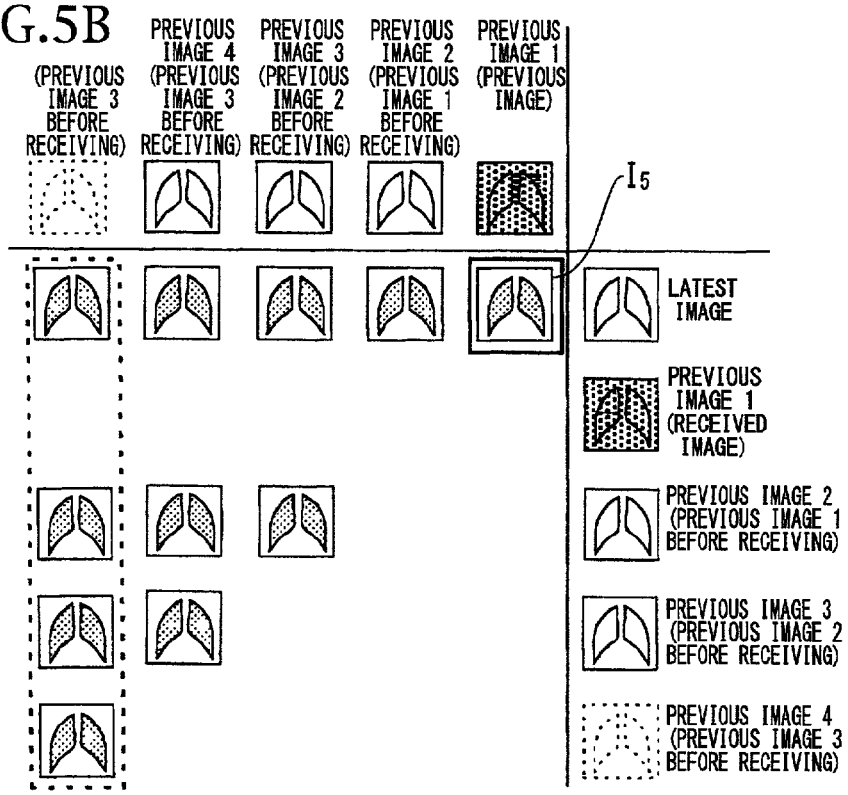
FIG. 5B is a conceptional view showing the example of the automatic producing information and the automatic deleting information by using the automatic producing method 2.

In method 2, the temporal subtraction image I5 is automatically produced according to only the pair of the received image and the latest image, as shown in FIG. 5B. In FIG. 5B, the temporal subtraction image I5 surrounded with a squared solid line is the temporal subtraction image to be automatically and newly produced under the condition that the number N of previous cases is 4, and the temporal subtraction images surrounded with a squared broken line are the temporal subtraction images to be automatically deleted by overflowing from the condition that the number N of previous cases is 4 because of the newly produced temporal subtraction images under the condition that the number N of previous cases is 4.

The receiving image is not only the latest chest image in time series, but also the receiving of the image data of the second order in time series is considered as this embodiment. Of course, it is possible that the receiving image is the latest chest image in time series. In this case, the temporal subtraction images are produced according to the pairs of the latest image and each of the previous images 1~4, and all temporal subtraction images produced to be paired with the previous image 4 before receiving are automatically deleted.

However, in a case where the received chest image is the fifth order or more in time series (in case of being older than the previous image 4), automatically producing the temporal subtraction image is not performed.

As described above, it is possible for the control unit 30 to produce the automatic maintenance information (the automatic producing information and the automatic deleting information) so that the produced automatic maintenance information is stored on the automatic maintenance information storage unit 60.

Figure 6:
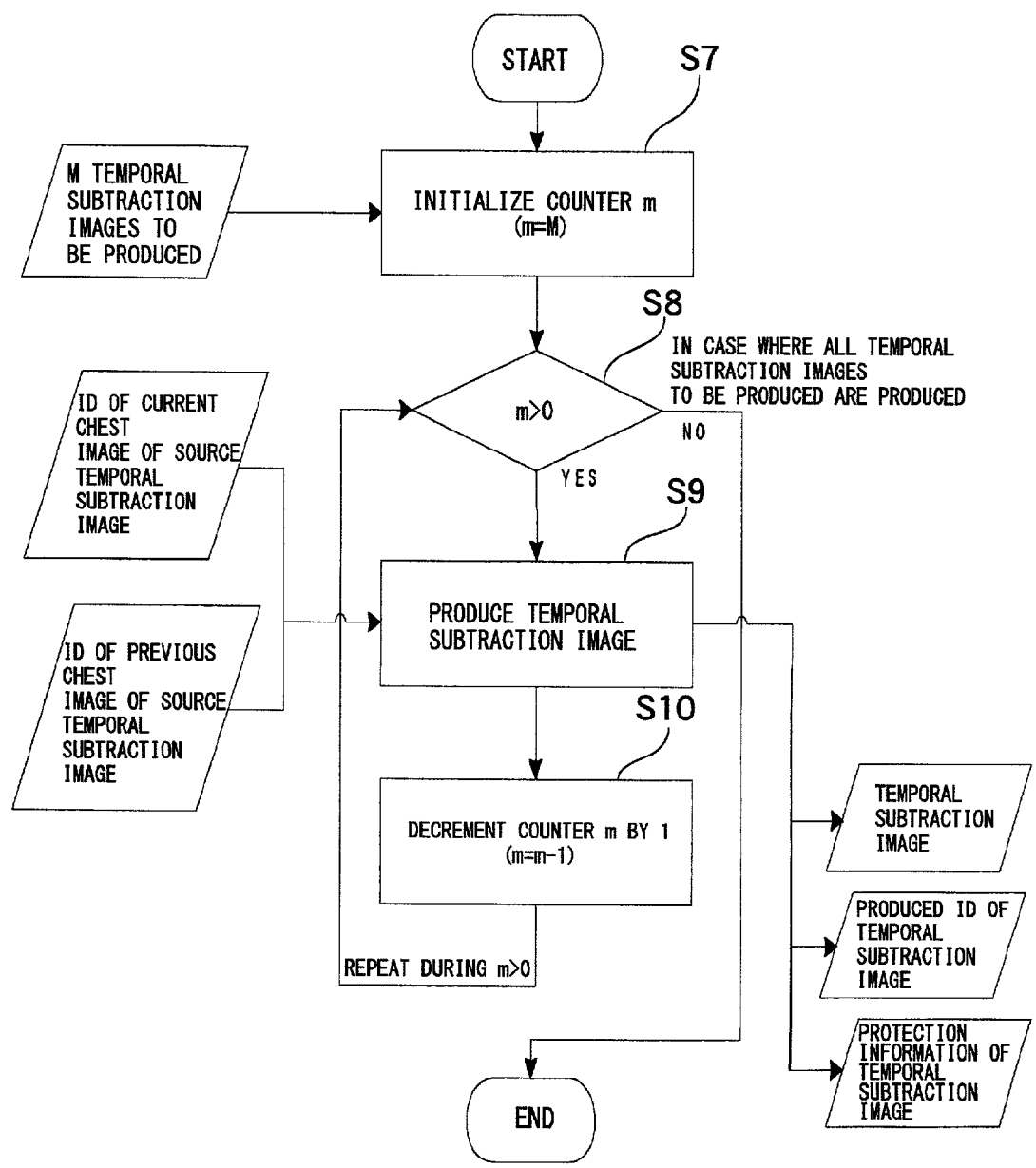
FIG. 6 is a flow chart showing a processing procedure of producing a temporal subtraction image by an automatic producing unit for a temporal subtraction image.

FIG. 6 shows a flowchart of the automatic producing procedures for the temporal subtraction images in the automatic producing unit 40.

(Step S7) Initialize Counter m

The automatic producing unit 40 has a repetition counter and initializes the repetition counter m with the number M of the temporal subtraction images to be produced so that counter m is set to M.

It is appreciated that M temporal subtraction images to be produced exists. Therefore, the producing process for the temporal subtraction images are repeated M times automatically.

(Step S8) m>0

It is determined by the producing unit 40 whether the automatic producing process is repeated M times or not, and in a case where the temporal subtraction images of all the pairs of the images corresponding to the automatic producing information stored on the storage unit 60 have been produced (m=0), the process is terminated.

On the other hand, in a case where the temporal subtraction images of all the pairs of the images corresponding to the automatic producing information have not been produced (m>0), the process of the producing unit 40 is shifted to step S9 and continues the process of producing the temporal subtraction images.

(Step S9) Producing the Temporal Subtraction Images

The producing unit 40 generates the ID of the temporal subtraction image (source ID) from the currently paired images of the source of the temporal subtraction image in the automatic producing information, and, on the basis of the generated source ID, the IDs of the paired current and previous chest images, produces the temporal subtraction image in accordance with the temporal subtraction method disclosed in Japanese Patent Publication No. 7-37074 or the like, so as to store the produced temporal subtraction image, the source ID corresponding thereto and the protection information thereof, respectively.

For example, by using, as the current chest image, the latest image, and, as the previous chest image, the previous image 1 (the received image), the temporal subtraction image I1 and the source ID ("the ID of the latest image +"#"+ the ID of the previous image 1") are produced by the producing unit 40, respectively.

At this time, the protection information is stored as "releasing". In a case where it is desired to protect the produced temporal subtraction image, the protection information must be "setting" by the protection setting/releasing unit 80 according to the instruction by the input device 81 as soon as storing to the image data storage unit 10 is completed.

In this embodiment, the source ID of the temporal subtraction image is produced by connecting the ID of the current chest image and the ID of the previous chest image with the character "#" (on condition that IDs of the paired images do not contain the character "#" and the connecting character may be selected depending on the use in the whole system). However, in the present invention, it is not limited to this structure, but the ID must be unique in this system.

In this case, a data storage area, such as a database, must be provided in the data storage unit 10, and it must be required to store on the data storage area the data indicating that the temporal subtraction image is produced by any one of the current chest image and any one of the previous chest image.

In this embodiment, since the respective IDs of the paired current and previous chest images can be obtained to be specified easily from the source ID of the temporal subtraction image, it is possible to provide a system which is very economical, thereby saving the data storage area in the data storage unit.

(Step S10) Decrement Counter by 1

The producing unit 40 counts the remaining number of the pairs of the current and previous images for producing the temporal subtraction images except for the at least one pair of the current and previous images already processed so as to decrement the counter m to set the counter m to m−1.

In this embodiment, the producing unit 40 performs to count the remaining number of the pairs of current and previous images, but the producing unit 40 may count the total number of the pairs of the source images which have already been subjected to the producing process.

Figure 7:
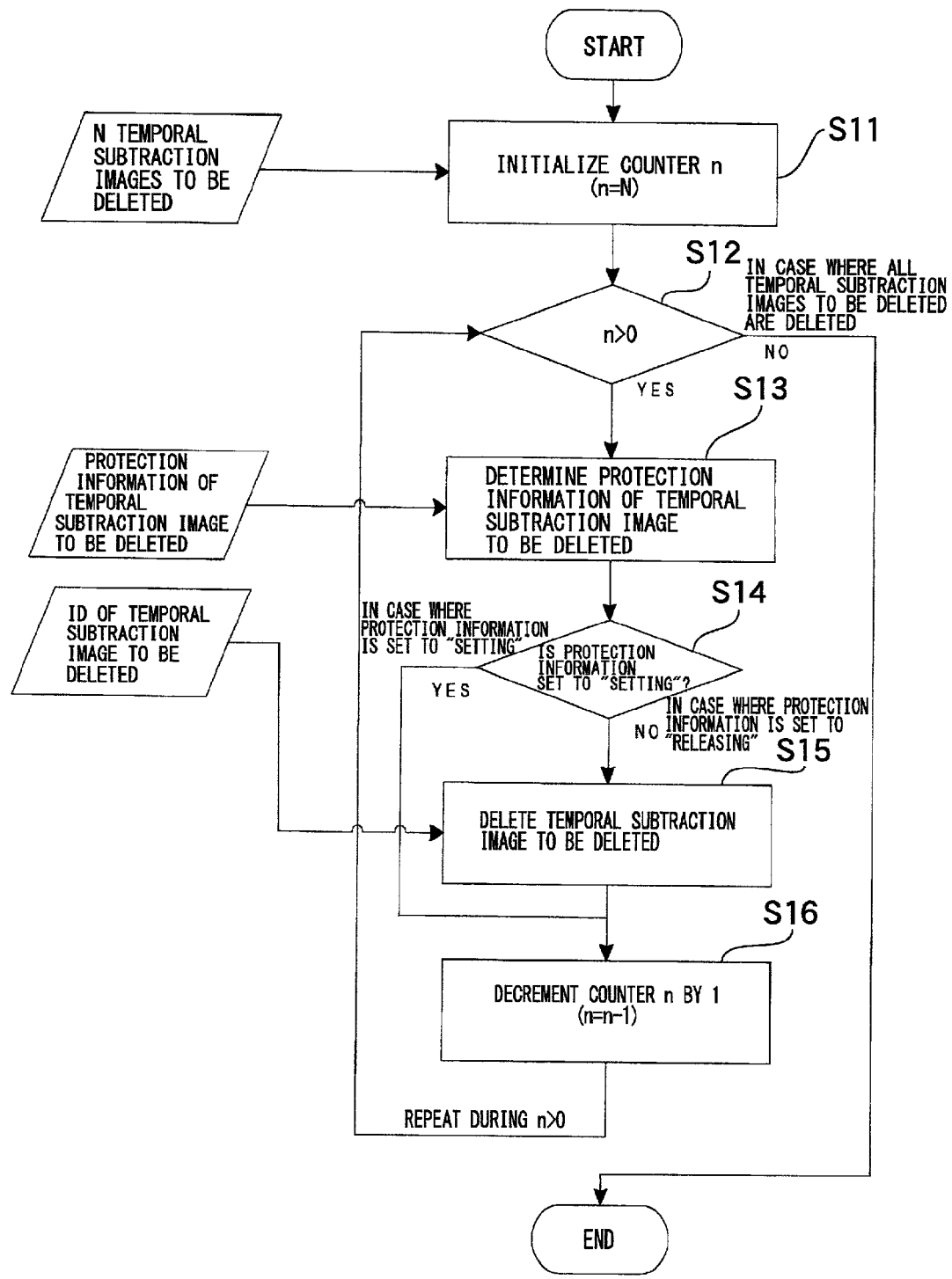
FIG. 7 is a flow chart showing a processing procedure of deleting a temporal subtraction image by an automatic deleting unit for a temporal subtraction image.

FIG. 7 shows a flowchart of the automatic deleting process for the temporal subtraction images in the automatic deleting unit 50.

(Step S11) Initialize Counter n

The automatic deleting unit 50 has a repetition counter and initializes the repetition counter n with the number N of the temporal subtraction images to be deleted so that counter n is set to N.

It is appreciated that N temporal subtraction images to be deleted exists in maximum. Therefore, the deleting process for the temporal subtraction images are repeated N times automatically.

(Step S12) n>0

It is determined whether the automatic deleting process is repeated N times or not, and in a case where all the temporal subtraction images to be deleted existed in the automatic deleting information have been deleted (n=0), the process is terminated.

On the other hand, in a case where all the temporal subtraction images to be deleted have not been deleted (n>0), the process is shifted to step S13 and the process continues of deleting the temporal subtraction images.

(Step S13) Protection Determination of the Temporal Subtraction Images to be Deleted.

Next, the deleting unit 50 determines whether the protection information is set to "setting" or to "releasing" in the protection information with reference to the temporal subtraction image, which is currently processed, to be deleted.

(Step S14) Is Protection Information Set to "setting"?

In step S14, in a case where the deleting unit 50 determines that the protect information is set to "releasing", the deleting unit 50 shifts in step S15 so as to delete the temporal subtraction image.

On the contrary, in step S14, in a case where the deleting unit 50 determines that the protect information is set to "setting", the process of the deleting unit 50 is shifted to step S16, without deleting the temporal subtraction image.

(Step S15) Deletion of the Temporal Subtraction Image to be Deleted

The deleting unit 50 deletes the currently processed temporal subtraction image from the data storage unit 10.

After deletion, the process of the deleting unit 50 is shifted to step S16.

(Step S16) Decrement Counter n by 1

The deleting unit 50 counts the remaining number of the pairs of the current and previous images for deleting the temporal subtraction images except for the at least one pair of the current and previous images already processed so as to decrement the counter n thereby setting the counter n to n−1.

In this embodiment, the deleting unit 50 performs so as to count the remaining number of the pairs of current and previous images, but the deleting unit 50 may count the total number of the pairs of the source images which have already been subjected to the deleting process.

While there has been described what is at present considered to be the preferred embodiments and modifications of the present invention, it will be understood that various modifications which are not described yet may be made therein, and it is intended to cover in the appended claims all such modifications as fall within the true spirit and scope of the invention.

What is claimed is:

1. A method for automatically producing a temporally processed image, the method comprising:
   preparing a storage unit, the storage unit storing thereon a plurality of radiographic images, the plurality of radiographic images being taken at different points of time;
   capturing a new radiographic image;
   automatically producing, in response to said capturing, a specified number of temporally processed images according to a predetermined number of pairs of the radiographic images, wherein the pairs of the radiographic images include the captured radiographic image, and wherein the predetermined number of pairs of the radiographic images are previously specified;
   attaching a first ID to each radiographic image in the storage unit as a first attribute information, wherein the first ID uniquely identifies each radiographic image stored in the storage unit;
   attaching a second ID to each existing temporally processed image stored in the storage unit as a second attribute information, wherein the second ID uniquely identifies each temporally processed image stored in the storage unit, and wherein the second ID comprises a pair of the first IDs corresponding to a respective pair of the radiographic images stored in the storage unit;

defining a third ID for each temporally processed image which is intended to be produced according to the predetermined number of pairs of the radiographic images stored in the storage unit, wherein the third ID comprises a pair of the first IDs corresponding to a respective pair of the radiographic images stored in the storage unit; and preventing overlapped production of a same temporally processed image stored in the storage unit by not producing a temporally processed image when the pair of the first IDs of the third ID of the temporally processed image which is intended to be produced overlaps the pair of the first IDs of one of the second IDs of the existing temporally processed images stored in the storage unit.

2. A method for automatically producing a temporally processed image according to claim 1, wherein the new captured radiographic image and the produced number of temporally processed images are stored on the storage unit.

3. A method for automatically producing a temporally processed image according to claim 2, further comprising, in response to said capturing, automatically deleting at least one of the temporally processed images from the storage unit, the at least one of the deleted temporally processed images becoming unnecessary.

4. A method for automatically producing a temporally processed image according to claim 3, wherein the at least one of the deleted temporally processed images is overflowed from the predetermined number of pairs of the radiographic images.

5. A method for automatically producing a temporally processed image according to claim 3, further comprising avoiding overflowing of data in the storage unit, wherein said avoiding comprises:

attaching a unique deleting priority to each temporally processed image in the storage unit;

calculating M, wherein M is the number of temporally processed images which are necessary to be produced in response to said capturing;

counting free space within a storage space of the storage unit for storing the temporally processed images, wherein the free space is represented by L and corresponds to a number of sheets of the temporally processed images; and designating a total number of K sheets of the temporally processed images counted in a descending order of deleting priories as unnecessary images when K>0 under an equation of K=M−L.

6. A method for automatically producing a temporally processed image according to claim 3, wherein a deleting priority is attached to each temporally processed image in the storage unit according to a rule, wherein the rule includes:

at a time when the temporally processed images in the storage unit are produced from pairs of first and second radiographic images, one of the temporally processed images produced from an older second radiograph image has a higher deleting priority, and at a time when one of the second radiograph images is used to produce the temporally processed images, one of the temporally processed images produced from an older first radiograph image has a higher deleting priority.

7. A method for automatically producing a temporally processed image according to claim 2, further comprising setting at least one of the temporally processed images stored on the storage unit to be protected so that the at least one of the protected images is prevented from being deleted, wherein the at least one of the protected images is permanently stored on the storage unit.

8. A method for automatically producing a temporally processed image according to claim 1, wherein the pairs of the radiographic images are composed so that a latest radiographic image and a predetermined number of previous radiographic images are paired, wherein the latest radiographic image is taken at a latest point of time, and wherein the predetermined number of previous radiographic images are taken at points of time sequentially before the latest radiographic image is taken.

9. A method for automatically producing a temporally processed image according to claim 8, wherein the pairs of the radiographic images are composed so that the new captured radiographic image is paired with a predetermined number of the radiographic images.

10. A method for automatically producing a temporally processed image according to claim 8, wherein, in a case where the new captured radiographic image is one of the previous radiographic images, the pairs of the radiographic images are composed so that the new captured radiographic image and the latest radiographic image are paired, and wherein, in a case where the new captured radiographic image is the latest radiographic image, the pairs of the radiographic images are composed so that the new captured radiographic image and the predetermined number of previous radiographic images are paired.

11. A method for automatically producing a temporally processed image according to claim 8, wherein the predetermined number of the paired radiographic images corresponds to a number of the previous radiographic images stored on the storage unit as previous cases.

12. A system for automatically producing a temporally processed image, the system comprising:

a storage unit which stores thereon a plurality of radiographic images, said plurality of radiographic images being taken at different points of time;

means for capturing a new radiographic image;

first production means for automatically producing, in response to the capture of the new radiographic image, information specifying a predetermined number of pairs of the radiographic images, wherein the specified predetermined number of pairs of the radiographic images includes the newly captured radiographic image; and second production means for automatically producing a specified number of temporally processed images according to the information produced by the first production means;

wherein a first ID is attached to each radiographic image in the storage unit as a first attribute information, the first ID uniquely identifying each radiographic image stored in the storage unit;

wherein a second ID is attached to each existing temporally processed image stored in the storage unit as a second attribute information, the second ID uniquely identifying each temporally processed image stored in the storage unit;

wherein the second ID comprises a pair of the first IDs corresponding to a respective pair of the radiographic images stored in the storage unit;

wherein a third ID is defined for each temporally processed image which is intended to be produced according to the predetermined number of pairs of the radiographic images stored in the storage unit;

wherein the third ID comprises a pair of the first IDs corresponding to a respective pair of the radiographic images stored in the storage unit; and wherein overlapped production of a same temporally processed image stored in the storage unit is prevented by not producing a temporally processed image when the pair of the first IDs of the third ID of the temporally processed image which is intended to be produced overlaps the pair of the first IDs of one of the second IDs of the existing temporally processed images stored in the storage unit.

13. A system for automatically producing a temporally processed image according to claim 12, wherein the new captured radiographic image and the produced number of temporally processed images are stored on the storage unit.

14. A system for automatically producing a temporally processed image according to claim 13, further comprising means for storing thereon the information produced by the first production means.

15. A system for automatically producing a temporally processed image according to claim 13, wherein the plurality of radiographic images are obtained from a patient by taking an image of the patient at different points of time, wherein the patient has identification information, wherein each of the radiographic images has identification information, wherein said storage unit stores the identification information of the patient related to each of the radiographic images and the temporally processed images, wherein said storage unit stores the identification information of each of the radiographic images and the temporally processed images, and each point of time at which of each of the radiographic images is taken, and wherein said first production means comprises:

a detecting unit for detecting that the new radiographic image is captured by the capturing means;

a unit for extracting the identification information of the patient corresponding to the new radiographic image detected by the detecting unit;

a unit for obtaining the identification information of the radiographic images, the points of time at which the radiographic images were taken, previous radiographic images from the storage unit, and the identification information of each of the radiographic images, wherein the points of time at which the radiographic images were taken and the previous radiographic images correspond to the extracted identification information of the patient, and wherein the previous radiographic images are previously stored on the storage unit; and a unit for producing the information specifying the predetermined number of pairs of the radiographic images according to a number of the previous radiographic images.

16. A system for automatically producing a temporally processed image according to claim 13, wherein said first production means determines whether or not one of the temporally processed images to be produced is stored on said storage unit, wherein in a case where the one of the temporally processed images has already been produced, the information specifying at least one of the pairs of the radiographic images is not produced.

17. A system for automatically producing a temporally processed image according to claim 13, wherein said first production means, in response to the capture of the new radiographic image, produces deleting information specifying at least one of the temporally processed images which becomes unnecessary, and wherein said system for automatically producing a temporally processed image further comprises means for automatically deleting, in response to the capture of the new radiographic image, at least one of the temporally processed images from the storage unit on the basis of the produced deleting information.

18. A system for automatically producing a temporally processed image according to claim 13, further comprising means for setting at least one of the temporally processed images stored on the storage unit to be protected so that the at least one of protected images is prevented from being deleted, and means for releasing the protected state of the at least one of the temporally processed images.

* * * * *